(12) United States Patent
Ma et al.

(10) Patent No.: US 7,840,044 B2
(45) Date of Patent: Nov. 23, 2010

(54) METHOD AND SYSTEM FOR LIVER LOBE SEGMENTATION AND PRE-OPERATIVE SURGICAL PLANNING

(75) Inventors: Feng Ma, Pennington, NJ (US); Guo-Qing Wei, Plainsboro, NJ (US); Li Fan, Belle Mead, NJ (US); Cheng-Chung Liang, West Windsor, NJ (US); Jianzhong Qian, Princeton Junction, NJ (US); Xiaolan Zeng, Princeton, NJ (US)

(73) Assignee: Edda Technology Inc., Princeton Junction, NJ (US)

( * ) Notice: Subject to any disclaimer, the term of this patent is extended or adjusted under 35 U.S.C. 154(b) by 966 days.

(21) Appl. No.: 11/590,904

(22) Filed: Nov. 1, 2006

(65) Prior Publication Data

US 2008/0103385 A1 May 1, 2008

Related U.S. Application Data

(60) Provisional application No. 60/731,939, filed on Nov. 1, 2005.

(30) Foreign Application Priority Data

Nov. 1, 2006 (WO) ............... PCT/US2006/042638

(51) Int. Cl.
*G06K 9/00* (2006.01)
*A61B 5/05* (2006.01)
(52) U.S. Cl. ...................................... 382/128; 600/416
(58) Field of Classification Search ................ 382/128, 382/129, 130, 131, 132, 133, 134, 164, 171–179; 600/141, 407, 410, 425, 516, 416; 378/4, 378/21–27, 101; 128/915, 920, 922
See application file for complete search history.

(56) References Cited

U.S. PATENT DOCUMENTS

| 6,249,594 B1 * | 6/2001 | Hibbard ..................... 382/128 |
| 7,356,367 B2 * | 4/2008 | Liang et al. ................. 600/407 |
| 7,519,209 B2 * | 4/2009 | Dawant et al. .............. 382/128 |

OTHER PUBLICATIONS

International Preliminary Report on Patentability and Written Opinion issued in corresponding International Application No. PCT/US2006/042638, dated May 15, 2008.
Dirk Selle et al., "Analysis of Vasculature for Liver Surgical Planning", vol. 21. No. 11, Nov. 2002.
Reinhard Beichel et al., "Liver Segment Approximation in CT Data for Surgical Resection Planning", XP-002431358.
Gerald Glombitza et al, "Virtual Planning of Liver Resections: Image Processing, Visualization and Volumetric Evaluation", International Journal of Medical Informatics. 53 (1999) 225-237.
Bernhard Reitinger et al, "Tools for Augmented Reality Based Liver Resection Planning". XP-002431359.
Search Report dated May 15, 2007.

* cited by examiner

*Primary Examiner*—Abolfazl Tabatabai
(74) *Attorney, Agent, or Firm*—McDermott Will & Emery LLP (57) ABSTRACT

A method and system is provided for image segmentation for liver objects. Segmentation is performed to obtain a first set of objects relating to liver. More than one types in association with one of the first set of objects are identified. Landmarks are identified based on the segmented first set of objects or the different types of one of the first set of objects. A second set of objects including liver lobes are segmented based on the landmarks.

25 Claims, 13 Drawing Sheets

METHOD AND SYSTEM FOR LIVER LOBE SEGMENTATION AND PRE-OPERATIVE SURGICAL PLANNING

RELATED APPLICATIONS

This application claims priority to U.S. patent application Ser. No. 60/731,939, filed on Jun. 24, 2005, which Application is incorporated herein in its entirety by this reference.

FIELD OF INVENTION

The present teaching relates to method for disease diagnosis and surgical planning. In particular, it relates to computer assisted interactive segmentation of medical anatomies for disease diagnosis and surgical planning.

DISCUSSION OF RELATED ART

Early detection and early treatment is a key to fight against liver cancer. With the advancement of modern imaging technologies, liver cancers may be detected at an early stage. Following its detection and diagnosis, liver cancers may be treated based on different treatment plans, for example, Radio Frequency Ablation and surgical resection. To perform such treatments, planning has to be made prior to the operation. In particular, the physical position of a lesion with respect to liver lobes, the spatial relationship with respect to major vessels and branches need to be visualized and analyzed. Tools that help to identify liver lobes, visualize the spatial relationship among lesions, lobes and vessels are much needed. A virtual surgical environment in which physician can plan and simulate surgical operations would also be very useful. Such tools may also be helpful in biopsy path planning.

Some conventional liver lobe segmentation techniques rely solely on the identification of portal venous system, e.g., D. Selle, B. Preim, A. Schenk, H.-O. Peitgen, "Analysis of vasculature for liver surgical planning", *IEEE Transactions on Medical Imaging*, Vol. 21, Nov. 11, 2002, pp. 1344-1357. In such conventional systems, lobes are segmented based on the identification of blood support regions of the portal vessel branches. A problem with this conventional approach is that the accuracy of lobe segmentation depends solely on the accuracy of the segmentation of the portal veins. In situations where the portal vein signal in an image is week, the segmentation of portal veins may fail, resulting in failure of lobe segmentation.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

In this teaching, techniques that combine portal venous system with hepatic vein system as well as other anatomical landmarks for lobe segmentation are disclosed. Methods and means that can help physician to simulate pre-operative surgery and to recall the simulation during actual operation are also disclosed.

Figure 1A:
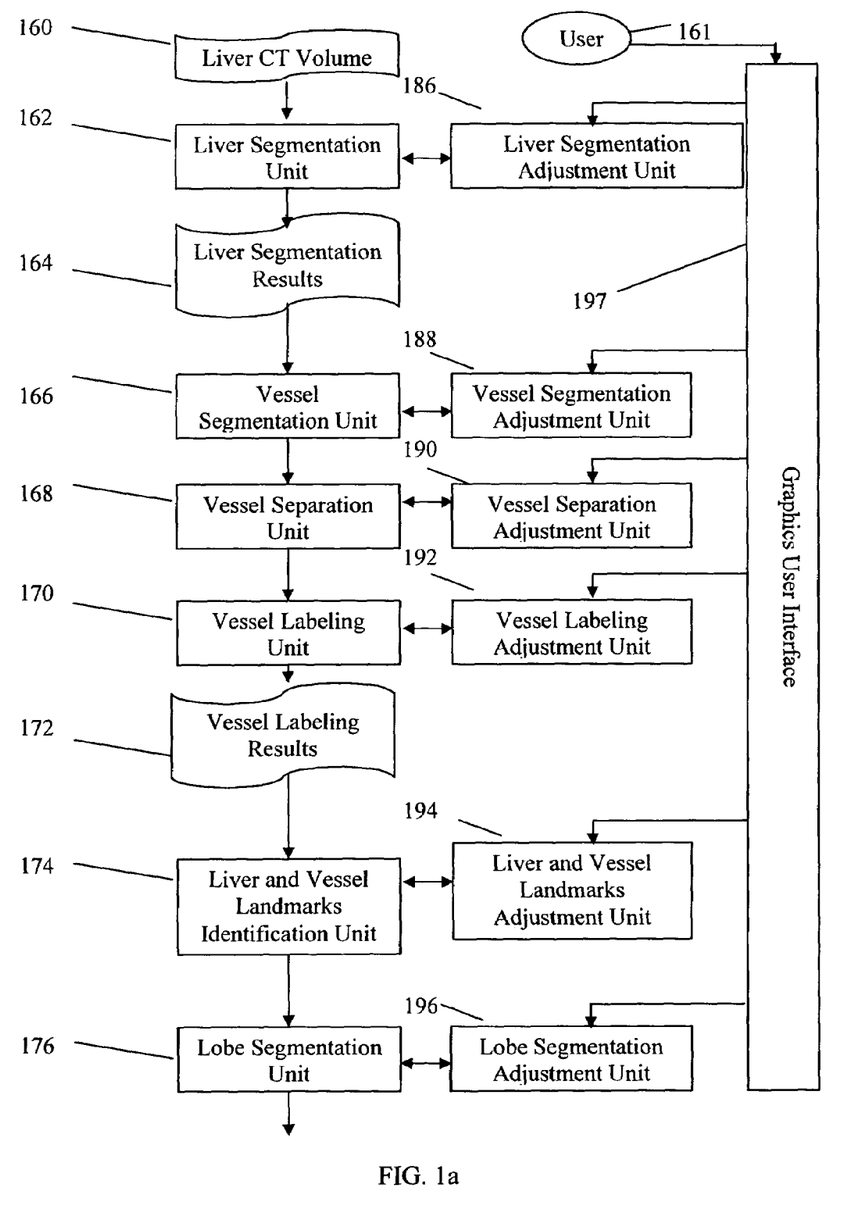
FIG. 1a shows a system diagram of liver lobe segmentation and surgical planning.

An exemplary diagram of an interactive liver lobe segmentation and surgical planning system is described in FIG. 1a. In this system diagram, liver CT volume 160 is the input to the system. A user 161 may interactive with the system through a graphics user interface 197. A liver segmentation unit 162, accepts liver CT volume as input and generates a liver mask. User may interactively adjust the liver segmentation results through a liver segmentation adjustment unit 186. The output of the liver segmentation unit may be represented as the liver segmentation results 164 and serves as inputs to subsequent modules. Taking liver segmentation results and liver CT volume as inputs, a vessel segmentation unit 166 may generate the 3D vessel system in liver CT volume. The vessel segmentation may be interactively adjusted by user through a vessel segmentation adjustment unit 188. The output of the vessel segmentation unit may be fed into a vessel separation unit 168. The vessel separation unit may identify various vessel systems in the liver and separate one from another. User may interactively assist the separation process through a vessel separation unit 190. Each separated vessel system may be labeled through a vessel labeling unit 170, according to relative spatial relationship of vessel segments. User may interactively adjust vessel labeling result through a vessel labeling adjustment unit 192. The output of the vessel labeling unit is the labeled vessel segments 172, according to their spatial locations and relationships. A liver and vessel landmarks identification unit 174 may, automatically or through certain user interactions, localize landmarks on liver surface or vessel. A user may interact with this unit through a liver and vessel landmarks adjustment unit 194. A lobe segmentation unit 176 may divide the liver into several lobe segments, based on the liver segmentation results, vessel labeling results and landmarks on liver and vessel. The output 178 of the lobe segmentation unit 176 may be either a complete or a partial segmentation of liver lobes according to the Couinaud's liver lobe definition described in the next paragraph. A user may interactively edit the liver lobe segmentation results through a lobe segmentation adjustment unit 196. A nodule segmentation unit 180 may segment out nodules from CT images. A user may interactively adjust the nodule segmentation result 182 through a nodule segmentation adjustment unit 198. Finally, a surgical planning unit 184 may assemble outputs of all previous segmentation modules and present users with information about liver, vessel, nodules and their relationships. A user may also interact with the surgical planning unit through graphics user interface 197 to obtain 3D spatial information, to plan surgery, and to perform virtual surgical operations.

Figure 1B:
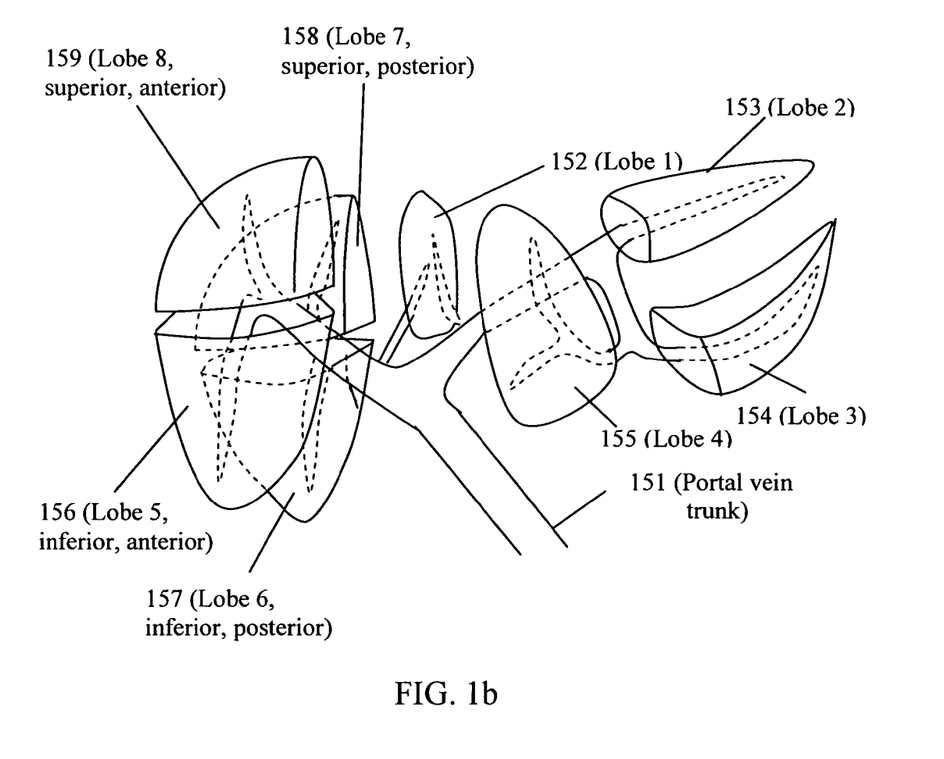
FIG. 1b illustrates the Couinaud's definition of liver lobes and their spatial relationship to vessels.

Liver lobes often play an important role such as being used as landmarks in surgical planning as to determination of resection regions. A widely adopted liver lobe segmentation scheme is the Couinaud's 8 segment system, as illustrated in FIG. 1b. In the Couinaud system, a liver is separated into 8 lobes, depicted as 152 to 159 in FIG. 1b. An individual piece of liver may be divided into left and right halves. The left half liver may comprise lobe 1 to 4. Lobes 2 and 3 are lateral to lobe 4. The right half liver may comprise lobes 5 to 8. Based on the spatial relationship among lobes, lobe 5 (156) may be called the inferior-anterior lobe, lobe 6 (157) the inferior-posterior lobe, lobe 7 (158) the superior-posterior lobe, and lobe 8 (159) the superior-anterior lobe. The portal vein system originated from portal vein trunk 151 may branch into each lobe. Portal vein branches inside lobe 1 to 8 may be labeled as portal vein branch 1 to 8, respectively.

Figure 1C:
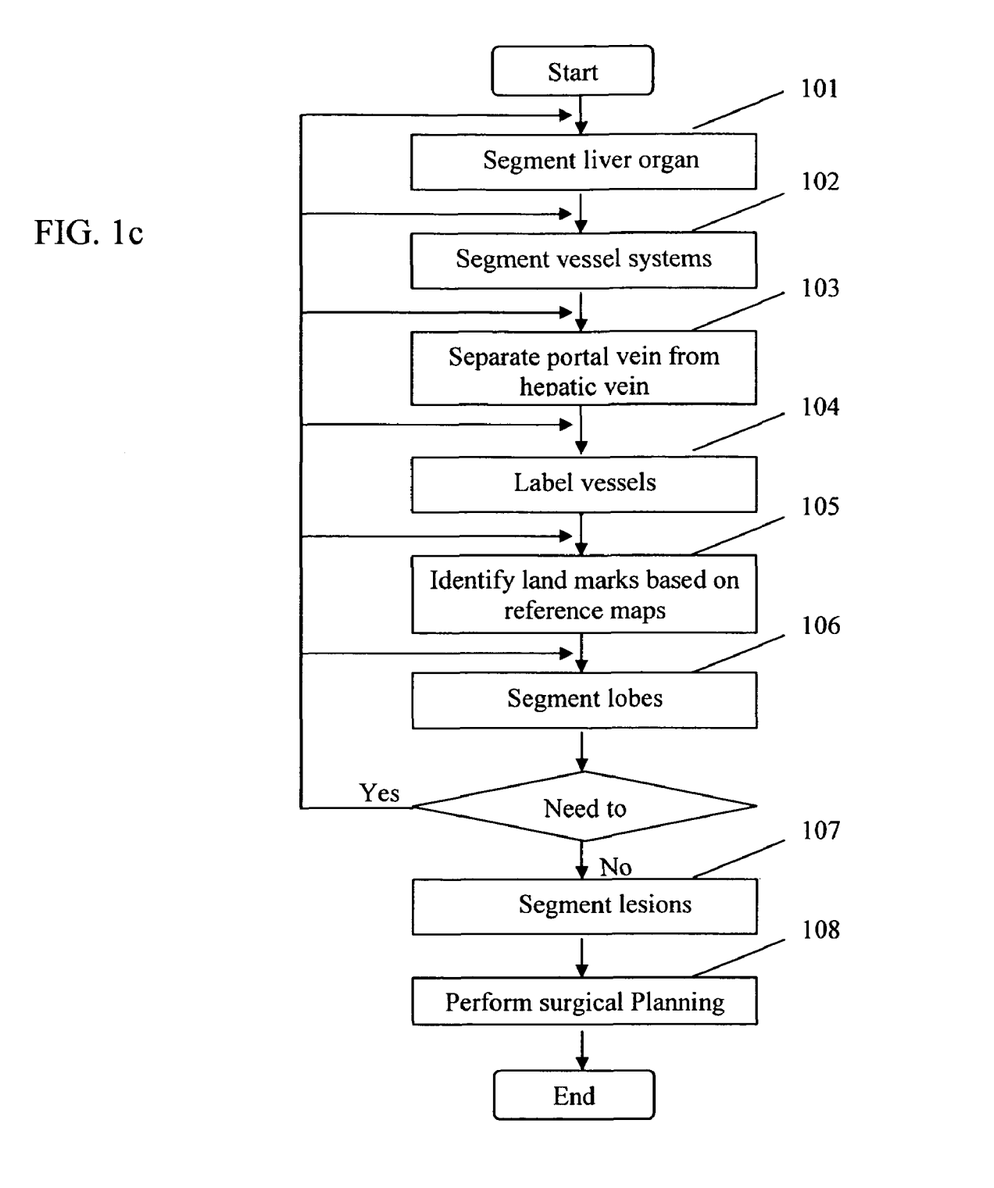
FIG. 1c shows an exemplary work flow for lobe segmentation and surgical planning, according to one embodiment of the present teaching.

An exemplary flowchart of an interactive liver lobe segmentation and surgical planning system is described in FIG. 1c. In this exemplary flowchart, liver volume is segmented from the abdominal CT image at step 101. Hepatic vessels are segmented interactively at step 102. Portal vein and hepatic vein system may be automatically or interactively separated at step 103. Vessel branches in the portal venous vessel system may be labeled as branches 1 to 8, as defined above. Hepatic vessel system may be labeled as left hepatic vein, middle hepatic vein and right hepatic vein. At step 104, the portal venous and hepatic vein system are labeled. Landmarks may be interactively or automatically identified at step 105. Such identified landmarks may be organized and visualized as a reference map, which may be utilized to guide the identification of different heptic veins. Liver lobes may then be segmented at step 106, based on the identified landmarks. Nodules in the liver may be automatically or interactively identified and segmented at step 107. Surgical planning may be performed, at step 108, based on the locations of lesion, liver lobes and vessels and their spatial relationship.

Figure 2:
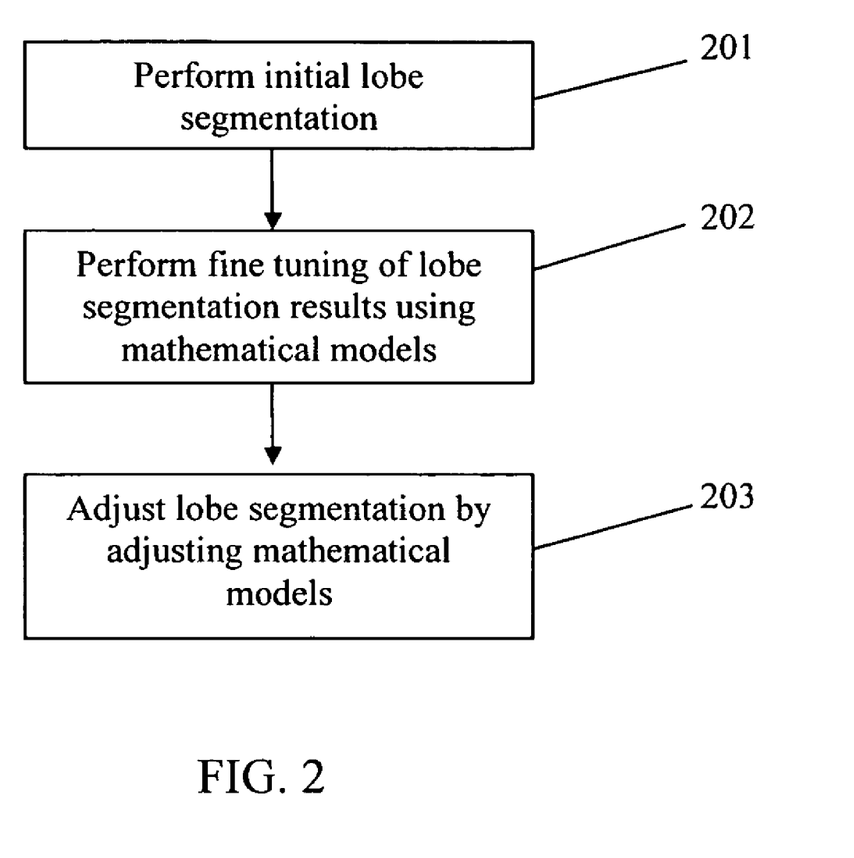
FIG. 2 shows an exemplary construct of a three-step method for lobe segmentation.

The step of liver lobe segmentation, at step 106, according to the current teaching, may be based on hybrid features obtained from labeled hepatic vein, portal vein, and other liver anatomical landmarks. The process of lobe segmentation may involve three steps in a coarse-to-fine manner, as illustrated in FIG. 2. The first step may be an initial segmentation of the liver lobes based on liver anatomical landmarks and portal venous vessel labeling, at step 201. The second step 202 may refine boundaries between lobes using mathematical models based on the initial lobe segmentation obtained at step 201, with additional information from hepatic veins and liver landmarks. Finally, boundary surfaces between lobes may be interactively fine-tuned in position and orientation, at step 203.

The hybrid lobe segmentation method as illustrated in FIG. 2 may be performed in different manners as discussed herein. Liver lobes may either be fully segmented, yielding 8 segments, or be partially segmented to result in one or more lobes of interest. Such segmentation may be performed in terms of a subset of features derived from hepatic vein, portal vein and liver landmarks.

At each step of lobe segmentation, the liver segmentation, vessel segmentation and vessel labeling may interact when it is needed. That is, at any step of lobe segmentation as shown in FIG. 2, users may switch to any of liver segmentation 101, vessel segmentation 102, vessel separation 103, vessel labeling 104, and landmark selection 105 steps to make any corrections and then continue the lobe segmentation.

Figure 3A:
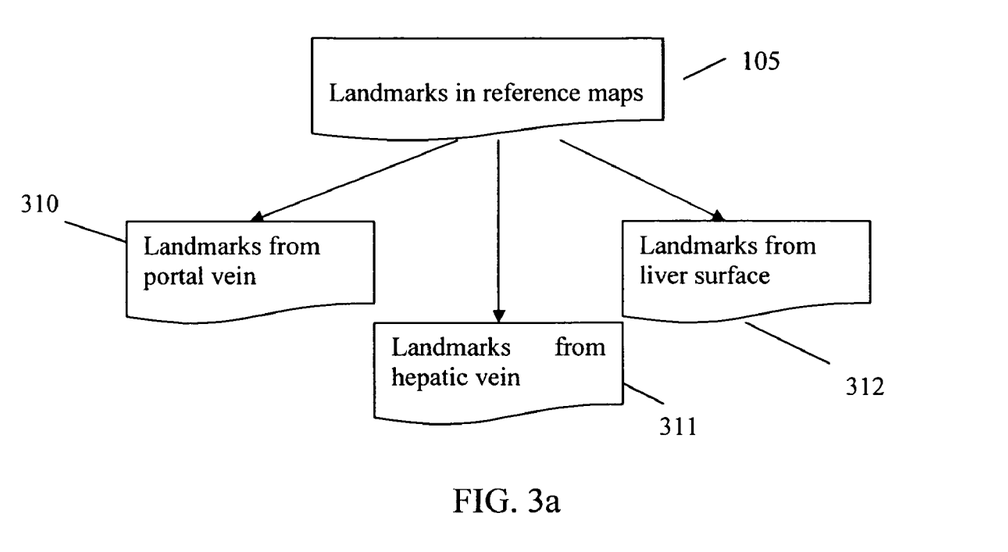
FIG. 3a illustrates of the hybrid landmark composition, according to the present teaching.

The lobe segmentation may be based on landmarks of different types. FIG. 3a illustrates 3 types of landmarks: landmarks from portal vein, 310, landmarks from hepatic vein, 311, and landmarks from liver surface, 312, according to the present teaching. These landmarks may be automatically identified or interactively selected. Such landmarks may be organized or visualized in the form of reference maps. Such references map may have built-in controls, that may be used to facilitate the interactive selection of landmarks. An exemplary embodiment is to label the respective landmarks by numeric numbers and embed controls within the numeric labels. A user may first click on a label using computer mouse in the reference maps, then click the corresponding landmark in the actual 2D or 3D visualization of the anatomies. The clicked place in 2D or 3D may show a symbol, such as a circle or a sphere in place to indicate a placed landmark. Landmarks that are placed in the reference map may be changed to a different color. The reference maps and corresponding anatomy may be visualized in either 3D or 2D or both.

Figure 3B:
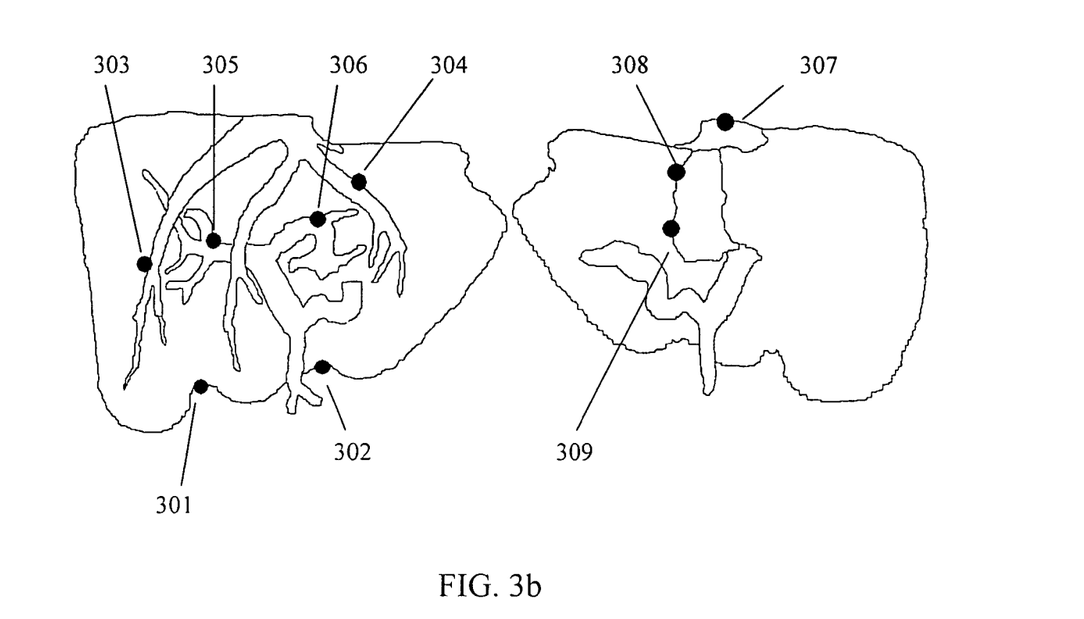
FIG. 3b shows an exemplary construct of a landmark reference map.

FIG. 3b illustrates an exemplary reference map. The landmark points may include a landmark on gallbladder fossa 301, a landmark on umbilical fissure 302, a landmark on inferior vena cava (IVC) 307, two landmarks on superficial ligamentum venosum 308 and 309. There may be two landmarks on the left and right hepatic veins, shown as 304 and 303, respectively. There may be also two landmarks on portal venous vessel, with one located on the main branch of right portal vessel tree 305, and the other located at the U-Point of the left portal vessel tree 306.

In addition to interactive identification of landmarks, such landmarks may also be automatically detected based on their geometric features and their spatial relationship to other anatomies. The automatically detected landmarks may be visually displayed on the respective positions in 3D or 2D. A user may use the reference control in the reference map to edit the automatically detected landmarks.

Figure 4:
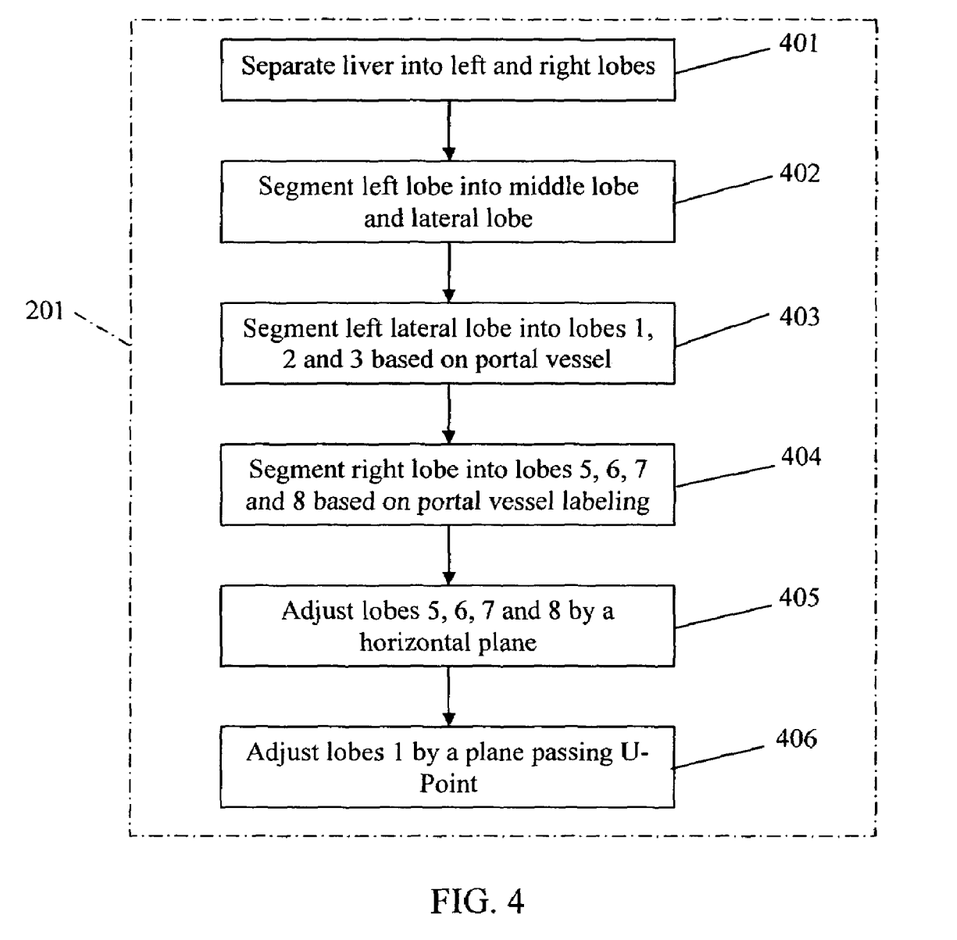
FIG. 4 shows an exemplary lobe segmentation flow chart.

The initial lobe segmentation, performed at 201, may be based on portal venous vessel labeling and liver landmarks. FIG. 4 is an exemplary flow chart of initial lobe segmentation. Liver may be separated into left and right lobes by a plane passing through IVC and gallbladder fossa, at step 401. The left and right liver lobes may be divided into 4 segments each independently. Left lobe may be separated into two parts, the middle lobe (lobe 4) and lateral lobe, by a plane passing IVC and umbilical fissure, at step 402. Based on the minimal distance to the labeled portal vessel branches 1, 2 and 3, the lateral lobe may be further divided into lobes 1, 2, and 3, at step 403. On the right side, based on the minimal distance to the labeled portal vessel branches 5 to 8, the right lobe may be separated into lobe 5, 6, 7 and 8, at step 404.

In the right liver, the boundary between superior lobes (7 and 8) and inferior lobes (5 and 6) may be adjusted by a horizontal plane passing the right portal vessel landmark, at step 405. After such adjustment, voxels in superior lobes 7 and 8 may be re-labeled as inferior lobes 6 and 5, respectively, if they are inferior to the horizontal plane, and vice versa. In the left liver, lobe 1 may be further adjusted with the plane passing the U-Point of the left portal vessel tree and two points on superficial ligamentum venosum, at step 406. Voxels that are in lobe 1 and lateral to the plane passing the U-Point of the left portal vessel tree will be re-labeled as lobe 2.

Figure 5:
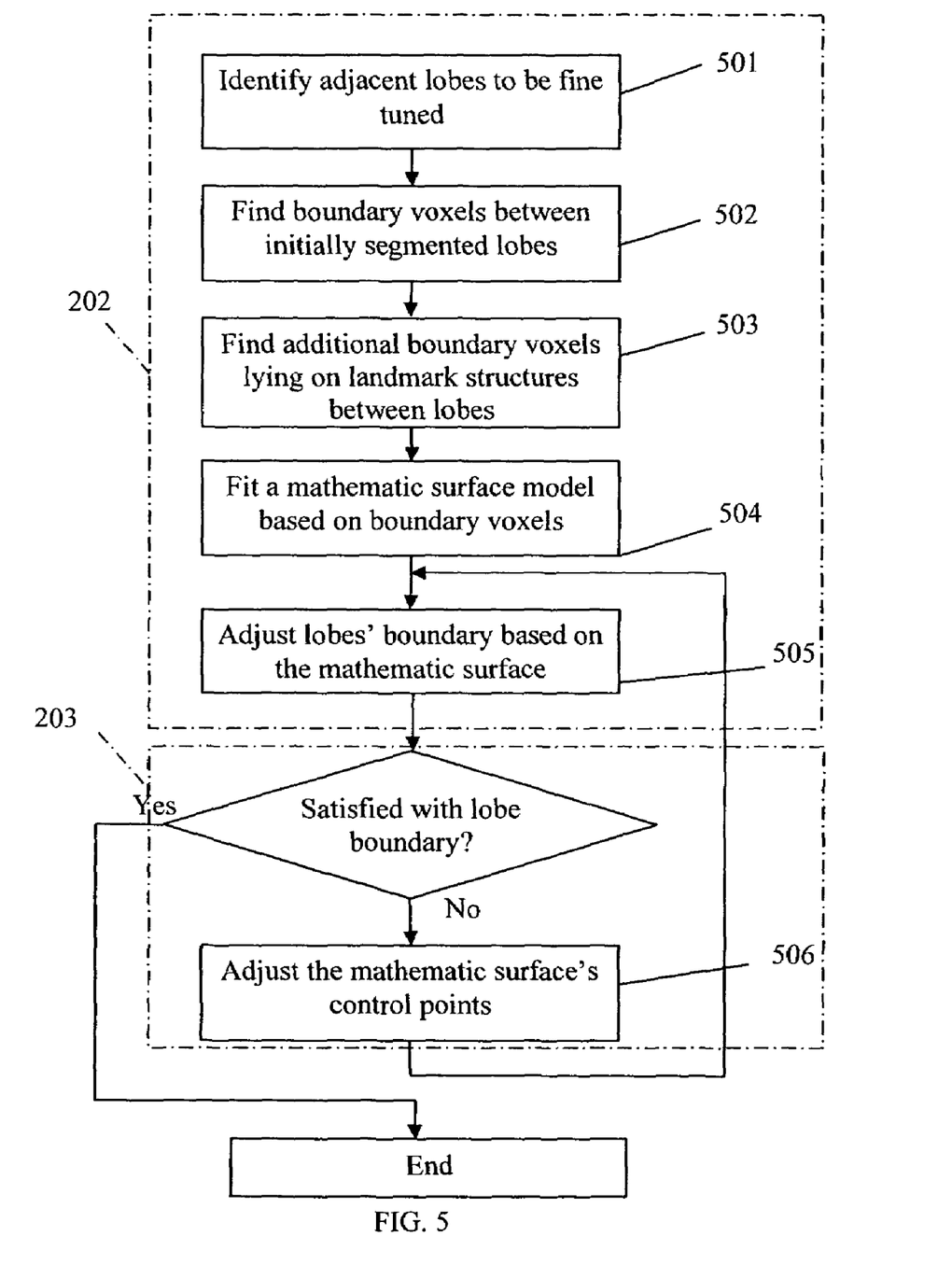
FIG. 5 shows an exemplary construct of an embodiment of the fine-tuning step of lobe segmentation.

After initial lobe segmentation, boundaries between certain lobes may be refined using mathematical models, with additional information from hepatic veins and other anatomical landmarks at step 202. Three steps may be involved in the fine tuning of a separation plane, as shown in FIG. 5. After adjacent lobes to be fine tuned are identified at step 501, boundary voxels between lobes may be extracted, at step 502. In addition, anatomical structures along lobe boundary surfaces may be extracted. Examples of such anatomical structure are the left and right hepatic veins. Voxels of the identified anatomical structure may be extracted and added into the boundary voxel set, at step 503. Furthermore, boundary voxels between lobes may be fitted with a mathematical surface model, e.g., a quadratic model, at step 504. This mathematical surface model may be used to adjust the boundary obtained in the initial step of lobe segmentation, at step 505. If user is not satisfied with the boundary, control points of the mathematical surface may be interactively adjusted at step 506.

Figure 6A:
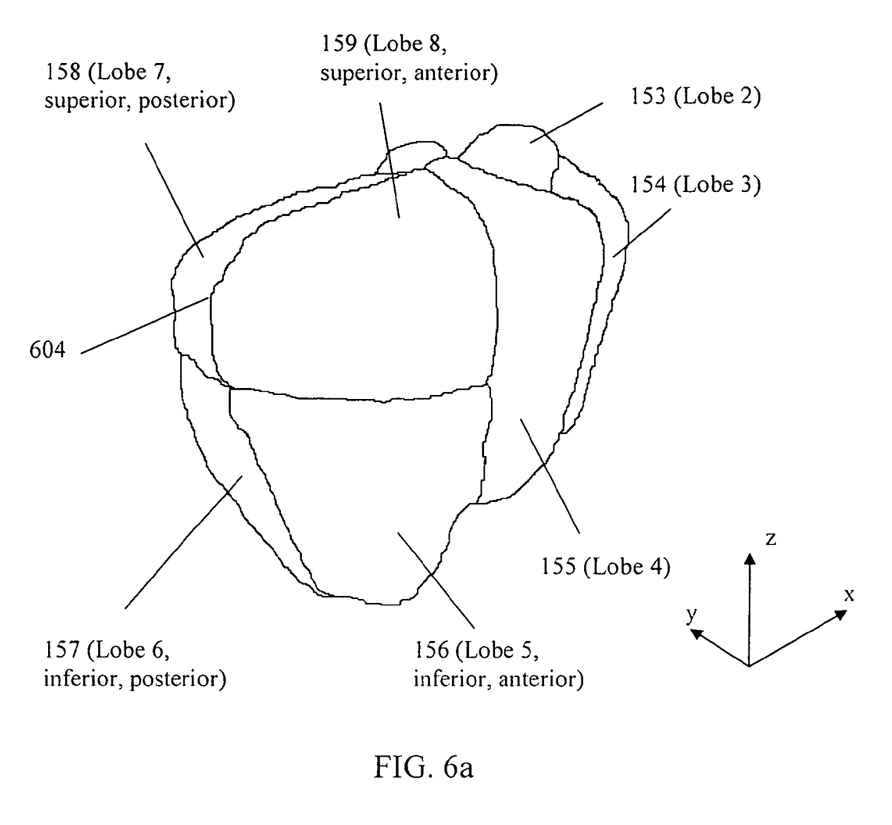
FIG. 6a and FIG. 6b illustrates an example of segmented liver lobes.
Figure 6B:
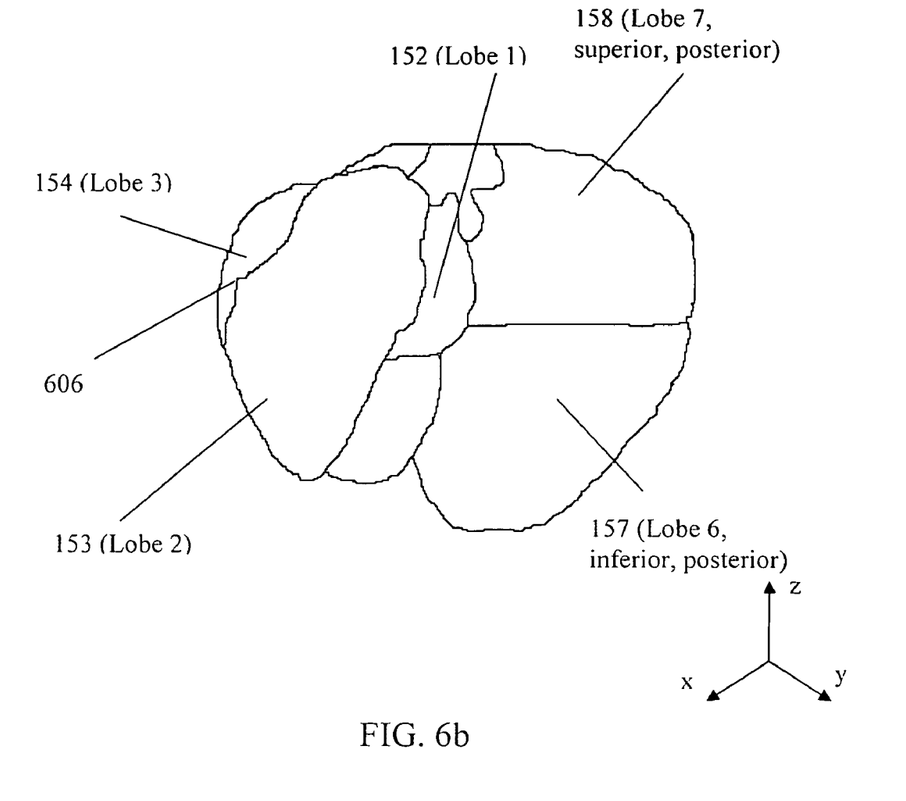

One example of lobe segmentation after fine tuning is shown in FIG. 6*a* (anterior view) and FIG. 6*b* (posterior view). In this example, there are eight lobes segmented according to the Couinaud's definition of liver lobes, indicated from 152 to 159. The boundary surface 604 between anterior lobes (156, 159) and posterior lobes (157, 158) in the right liver, may be modeled with a quadratic surface. The right hepatic vein, which may be automatically or interactively identified, may be used to fit the separation surface with the quadratic model. Voxels of anterior lobes (156, 159) may be re-labeled as posterior lobes (157, 158), respectively, if they lie posterior to the quadratic surface, and vice versa. The same method may be applied to the boundary surface between lobes 153 and 154 in the left liver, illustrated as 606 in FIG. 6*b*.

The mathematical model for surface fitting described above may be based on a surface with control points. Examples of a surface with control points are a B-spline surface or a non-uniform rational B-spline surface (NURBS). Positions of estimated control points may be adjusted in 3D to change the orientation and position of the surface model.

The segmentation of lobe 1 obtained at step 406 may also serve as an initialization of a deformable model, such as a 3D active contour model, to fine tune the boundary between lobe 1 and surrounding lobes.

If a user is interested in only some specific parts of liver lobes, or if the user chooses to label only some of the preferred vessels or landmarks, liver lobes may be segmented partially. One situation of partial lobe segmentation is when there is no hepatic vein available and when portal vessel branches 1 to 4 are unable to be segmented, e.g, due to insufficient contrast in CT images. In this case, only lobes 5 to 8 may be segmented.

Segmented liver lobes may be interactively adjusted at step 203. An adjustment may be made directly in the space of the boundary surface between lobes. By dragging certain control points on the boundary surface along a desired adjustment direction, the boundary surface may be modified to certain desired locations and/or orientations. A boundary surface may also be adjusted with a reference to an image space. For example, by placing certain anchor points on the image planes of some selected locations, a restriction may be enforced to force a boundary surface to pass these anchor points. Elasticity and smoothness of the surface may also be adjusted so that a desired degree of smoothness of a surface may be achieved. An adjustment may also be made by simplifying a boundary surface in terms of a simple surface, such as an approximated plane. An adjustment made with respect to a simple surface in terms of position and/or orientation may be used to achieve an approximate placement of the boundary surface. The approximate placement of the simple surface may be used as a weighting factor in a global optimization function that determines the final boundary surface.

The process of liver segmentation, vessel segmentation, separation of portal vein and hepatic vein, vessel labeling, landmark point selection and lobe segmentation may be a sequence of operations performed in order to achieve the final lobe segmentation. Any one of these operations may be modified in any order. If one operation is modified, the remaining operation may be executed as necessary to adjust the affected regions accordingly. For example, if portal vessel branch 5 and 8 were re-labeled after lobe segmentation, lobes 5 to 8 will be re-segmented to achieve results corresponding to latest vessel labels. Lobes 1 to 4 will be intact since modification of vessel branch 5 and 8 will not affect lobes 1 to 4.

Certain steps in the above processing scheme may be optional. When certain steps are opted out or skipped, a user may still continue other steps to accomplish lobe segmentation. For example, vessel segmentation may be omitted for some data due to poor image contrast. In this situation, user may be able to obtain the final lobe segmentation with landmarks identified either automatically or interactively.

Figure 7:
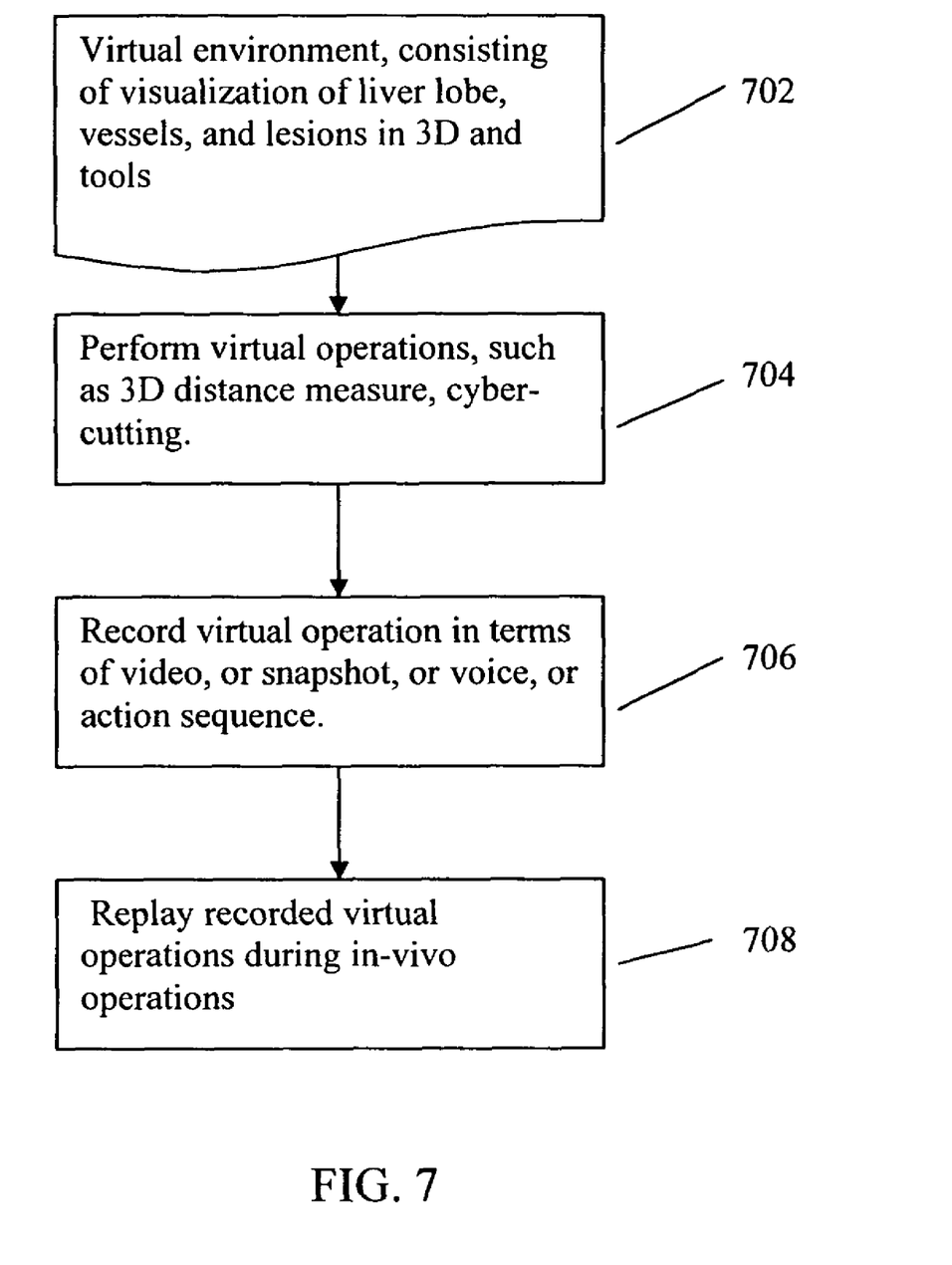
FIG. 7 shows an exemplary surgical planning flowchart.

The labeled lobes, vessels and segmented lesions may be used to establish a virtual environment for physicians to perform pre-operative surgical planning and to guide the in-vivo surgical operations. FIG. 7 illustrates an exemplary workflow of surgical planning according to the present teaching. The segmented liver lobes, liver vessel systems, together with identified lesions, may be visualized in 3D using a 3D render technique to reveal spatial relationship to users, at step 702. A set of toggle buttons or icons may be placed at a control panel, with each button/icon corresponding to the individual lobes, labeled vessels, and identified lesions. By toggling a selected button/icon, the 3D display of the corresponding anatomy may become transparent, hidden, or visible. Different combinations may be used to visualize a subset of selected anatomies and their spatial relationship. At step 704, physicians may perform virtual operations using tools provided by the system. The steps associated with a physician's operations may be recorded, at step 706, and such recording may be performed in different medium form such as a video clip, a screen snapshot, voice recording, or an action sequence. An action sequence may be defined as a sequence of operations and keystrokes recorded by computer so that a playback can be made based on this sequence. The recorded surgical steps in the virtual environment may be played back in different formats during in-vivo operation, at step 708. The playback may either be performed in the form of a video playback, paper printout of screenshots, voice playback, or playback of action sequence by computer.

Figure 8:
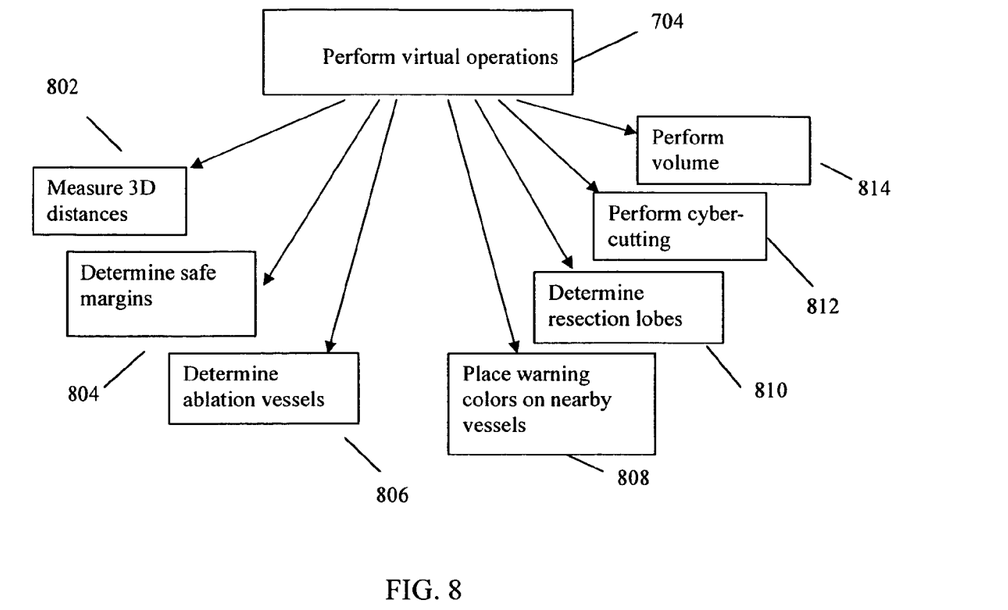
FIG. 8 shows an exemplary construct of virtual operations performed in surgical planning.

FIG. 8 illustrates an exemplary construct of the virtual operations that may be performed by physicians, according to step 704 of FIG. 7. The 3D operations may include 3D distance measure between any selected anatomies, at step 802. By clicking a "3D distance" button, or pressing a pre-defined hot key, the system may enter into the state of 3D distance measurement. The physician may click any point in the 3D display to designate the starting point of the measurement. Holding and dragging the mouse to any point in 3D display may give instant display of the distance measurement from the starting point to the current point. The physician may also perform the shortest distance measure from a selected lesion to any selected anatomy. By clicking on the lesion and the interested anatomy, e.g., the boundary surface between lobes, the system may perform automated computation of the shortest distance. An area on the surface containing the point of the shortest distance to the lesion may be colored differently than the surface itself. Such distance measurement tools may be used for finding the best path for cutting or for best entrance point for needle placement in biopsy.

At step 804, users may determine a safe margin around a lesion to be resected. By clicking a "Safe Margin" button, or pressing a hot key defined, a spherical surface may be placed around the lesion, with the lesion center being the sphere center. The radius of the sphere may be adjusted by dragging a sliding bar. The position of the spherical surface may be used as the safe margin in resection or in Radio Frequency Ablation treatment.

At step 806, users may click on a "Cyber-knife" button, or pressing a hot key defined, to enter into the virtual cutting status. The orientation of the knife may be controlled by a computer mouse. A cutting depth may be defined and adjusted along the orientation of the cyber knife through a sliding bar or by clicking on a control button. The trajectory of the cutting may be defined by drawing on the liver surface by users. The surface that is cut may be visualized transparently or may be removed. Multiple cuts may be performed using the same control steps.

At step 808, vessels passing through the volume within the safe margin of the nodules may be interactively or automatically labeled as ablation vessel branches. Ablation vessels are to be cut and ligated during surgery or treatment. A specific mark may be put on the cutting section of such vessels. Suggestions to surgeons as to the type of operations for such vessels may be displayed as text beside the cutting positions.

At step 808, major vessel branches close to ablation vessels may be labeled in warning colors to raise attentions. Physician may put annotations at any cutting positions by entering notes beside the cutting places.

At step 810, lobes to be removed or treated may be interactively or automatically identified based on lesion locations, their safe margins, and the spatial relationship between lesions and lobes.

At step 812, cyber-cutting may be performed through the GUI 197. User may control the cyber-knife to cut the 3D objects segmented, such as liver, vessel and lobes.

At step 814, physicians may perform volume measurements on liver lobes, on the cut and remaining parts of the liver. A physician may select the interested part to be measured and then click a 'volume measurement' button. The measured volumes may be displayed instantly on the screen beside the measured part in text. It may also be automatically added to a clinical report.

While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

What is claimed is:

1. A computer-implemented method, comprising:
    performing 3D segmentation to obtain a first set of objects including a 3D liver and one or more 3D vessels;
    identifying at least one type of vessels in the first set of objects, including a portal vein and a hepatic vein;
    identifying at least one 3D anatomic landmark point and/or structure based on the 3D liver and/or the at least one type of vessels in accordance with a 3D reference map; and
    obtaining, via 3D segmentation, a second set of objects which includes one or more 3D liver lobes based on the identified at least one 3D anatomic landmarks point and/or structure.

2. The method of claim 1, further comprising providing a virtual surgical planning setting based on at least one of:
    the first set of objects;
    the more than one type of one of the first set of objects;
    the landmarks; and
    the second set of objects.

3. The method of claim 2, wherein in the virtual surgical setting, one or more virtual operations are to be performed.

4. The method of claim 3, wherein an object can be visualized in the virtual surgical setting, wherein the visualized object includes at least one of:
    the first set of objects; and
    the second set of objects.

5. The method of claim 4, wherein the object to be visualized is presented in a manner that preserve spatial relationships with other objects with respect to a certain perspective.

6. The method of claim 4, wherein the object to be visualized can be rotated and translated in a 3D rendering space.

7. The method of claim 4, wherein the object to be visualized is presented with a label.

8. The method of claim 3, wherein the one or more virtual operations can be carried out with respect to a manipulable object.

9. The method of claim 8, wherein the manipulable object includes at least one of:
    a surface area close to the liver;
    the liver;
    a lobe;
    a vessel; and
    a nodule.

10. The method of claim 8, wherein the one or more virtual operations include at least one of:
    a surgical cut;
    a removal of at least a portion of the manipulable object; and
    manipulation of the manipulable object.

11. The method of claim 8, wherein, in carrying out a virtual operation, at least one reaction is generated.

12. The method of claim 11, wherein the at least one reaction includes:
    a measure made with respect to the virtual operation;
    an event detected that occurs as a result of the virtual operation;
    a response generated to indicate a resolution to the event detected; and
    a recording produced with respect to the virtual operation.

13. The method of claim 12, wherein the measure includes at least one of:
    a position measure indicating a position that is being affected by the virtual operation;
    a size measure indicating a size of an area that is being affected by the virtual operation;
    a distance measure between the position of the area and another object; and
    a safe margin determined based on the distance measure.

14. The method of claim 12, wherein the event includes at least one of:
    an opening occurring in an area that is being affected by the virtual operation;
    a change in relative spatial relationship between or among different objects;
    a disconnect of an object resulted from the virtual operation;

an ablation of a vessel;
a resection of a lobe; and
a consequence of the opening or the disconnect.

15. The method of claim 12, wherein the response includes at least one of:
    a message indicating an effect caused by the virtual operation;
    a first suggested solution to minimize the effect;
    a second suggested solution to maximize the effect;
    a warning to adopt a measure to eliminate the effect.

16. The method of claim 12, wherein the recording is at least one of:
    a video clip;
    an action sequence;
    a snapshot;
    a textual recording;
    a voice recording; and
    any combination thereof.

17. The method of claim 16, wherein the recording is made by appending a recording of the virtual operation to a different recording made with respect to a previous virtual operation.

18. A computer-implemented method, comprising:
    providing a virtual surgical planning setting;
    performing one or more virtual surgical operations in the virtual surgical planning setting, wherein
    the one or more virtual surgical operations are performed with respect to a plurality of objects related to liver,
    the plurality of objects include a first set of objects and a second set of objects,
    the first set of objects includes a 3D liver and one or more 3D vessels and at least one type of vessels, including a portal vein or a hepatic vein, and
    the second set of objects includes a liver lobe segmented based on at least one 3D anatomic landmark point and/or structure identified based on the 3D liver and/or the at least one type of vessels in accordance with a 3D reference map.

19. A system, comprising:
    a first segmentation unit configured for performing segmentation to obtain a first set of objects including a 3D liver and one or more 3D vessels;
    an identification unit configured for identifying at least one type of one of the first set of objects, including a portal vein or a hepatic vein;
    a landmark identification unit configured for identifying at least one 3D anatomic landmark point and/or structure based on the identified 3D liver and/or the at least one type of vessels in accordance with a 3D reference map; and
    a second segmentation unit configured for segmenting a second set of objects which includes one or more 3D liver lobes obtained based on the identified at least one 3D anatomic landmarks point and/or structure.

20. The system of claim 19, further comprising a surgical planning unit configured for providing a virtual surgical planning setting based on at least one of:
    the first set of objects;
    the more than one type of one of the first set of objects;
    the landmarks; and
    the second set of objects.

21. The system of claim 20, further comprising a virtual operating unit configured for facilitating one or more virtual operations to be performed in the virtual surgical planning setting.

22. A system, comprising:
    a first means for performing segmentation to obtain a first set of objects including a 3D liver and one or more 3D vessels;
    a second means for identifying at least one type of vessels in the first set of objects, including a portal vein or a hepatic vein at user's selection;
    a third means for identifying least one 3D anatomic landmark point and/or structure based on the identified 3D liver and/or the at least one type of vessels in accordance with a 3D reference map; and
    a fourth means for obtaining, via 3D segmentation, a second set of objects, which includes one or more 3D liver lobes obtained based on the identified at least one 3D anatomic landmark point and/or structure.

23. A system, comprising:
    a surgical planning unit configured for providing a virtual surgical planning setting;
    a virtual operating unit configured for facilitating one or more virtual surgical operations in the virtual surgical planning setting, wherein
    the one or more surgical operations are performed with respect to a plurality of objects relating to liver,
    the plurality of objects relating to liver include a first set of objects and a second set of objects,
    the first set of objects includes a 3D liver and one or more 3D vessels and at least one type of vessels, including a portal vein or a hepatic vein, and
    the second set of objects includes a liver lobe segmented based on at least one 3D anatomic landmark point and/or structure identified based on the 3D liver and/or the at least one type of vessels in accordance with a 3D reference map.

24. A system, comprising:
    a first means for providing a virtual surgical planning setting;
    a second means for facilitating one or more virtual surgical operations in the virtual surgical planning setting, wherein
    the one or more surgical operations are performed with respect to a plurality of objects related to liver,
    the plurality of objects related to liver include a first set of objects and a second set of objects,
    the first set of objects includes a 3D liver and one or more 3D vessels and at least one type of vessels, including a portal vein or a hepatic vein, and
    the second set of objects includes a liver lobe segmented based on at least one 3D anatomic landmark point and/or structure identified based on the 3D liver and/or the at least one type of vessels in accordance with a 3D reference map.

25. A non-transitory computer-readable medium having data recorded thereon, the data, when accessed, causing the machine to carry out the following:
    performing segmentation to obtain a first set of objects relating to liver;
    identifying more than one type of one of the first set of objects;
    identifying landmarks based on the first set of objects or the more than one type of one of the first set of objects; and segmenting a second set of objects, wherein the second set of objects includes liver lobes obtained based on the landmarks;

performing 3D segmentation to obtain a first set of objects including a 3D liver and one or more 3D vessels;

identifying at least one type of vessels in the first set of objects, including a portal vein and a hepatic vein at user's selection;

identifying at least one 3D anatomic landmark point and/or structure based on the 3D liver and/or the at least one type of vessels in accordance with a 3D reference map; and obtaining, via 3D segmentation, a second set of objects which includes one or more 3D liver lobes based on the identified at least one 3D anatomic landmarks point and/or structure.

* * * * *